(12) United States Patent
Chen et al.

(10) Patent No.: US 8,741,448 B2
(45) Date of Patent: Jun. 3, 2014

(54) FULLERENE DERIVATIVES AND OPTOELECTRONIC DEVICES UTILIZING THE SAME

(75) Inventors: Chih-Ping Chen, Kaohsiung County (TW); Yeu-Ding Chen, Miaoli County (TW); Shih-Ching Chuang, Hsinchu (TW); Yu-Wei Lin, Taichung (TW); Fu-Wei Chan, Changhua County (TW)

(73) Assignee: Industrial Technology Research Institute, Hsinchu (TW)

( * ) Notice: Subject to any disclaimer, the term of this patent is extended or adjusted under 35 U.S.C. 154(b) by 430 days.

(21) Appl. No.: 13/206,249

(22) Filed: Aug. 9, 2011

(65) Prior Publication Data

US 2012/0305919 A1 Dec. 6, 2012

(30) Foreign Application Priority Data

May 30, 2011 (TW) .............................. 100118816 A

(51) Int. Cl.
| | | |
|---|---|---|
| H01L 51/50 | (2006.01) | |
| H01L 29/786 | (2006.01) | |
| H01L 33/36 | (2010.01) | |
| C07D 409/14 | (2006.01) | |
| C07D 409/10 | (2006.01) | |

(52) U.S. Cl.
USPC .................. 428/690; 257/40; 257/57; 257/66; 257/E29.273; 428/917; 549/59; 549/12; 544/338

(58) Field of Classification Search
None
See application file for complete search history.

(56) References Cited

U.S. PATENT DOCUMENTS

| | | | |
|---|---|---|---|
| 6,479,111 | B2 | 11/2002 | Dykes et al. |
| 6,586,069 | B2 | 7/2003 | Dykes et al. |
| 6,743,481 | B2 | 6/2004 | Hoehn et al. |
| 7,435,403 | B2 | 10/2008 | Kronholm et al. |
| 7,476,375 | B1 | 1/2009 | Miller |
| 7,833,497 | B2 | 11/2010 | Kronholm et al. |
| 8,217,260 | B2 | 7/2012 | Laird et al. |
| 2008/0206222 | A1 | 8/2008 | Miwa et al. |
| 2008/0317658 | A1 | 12/2008 | Miller |
| 2008/0319207 | A1 | 12/2008 | Laird et al. |
| 2009/0154630 | A1 | 6/2009 | Miller |
| 2010/0163103 | A1 | 7/2010 | Wang et al. |
| 2010/0219385 | A1 | 9/2010 | Miller |
| 2010/0249168 | A1 | 9/2010 | Kronholm et al. |

FOREIGN PATENT DOCUMENTS

| | | |
|---|---|---|
| CN | 101529610 | 9/2009 |
| TW | 200812128 A | 3/2008 |
| TW | 200826305 | 6/2008 |
| TW | 200927787 | 12/2008 |
| TW | 200915583 | 4/2009 |
| TW | 201040208 | 5/2009 |

OTHER PUBLICATIONS

Vougioukalakis et al. "Open-cage fullerenes: towards the construction of nanosized molecular containers" Chem. Soc. Rev. 2010, 39, 817-844. Date of web publication: Nov. 16, 2009.*
Sonmez et al. "The Unusual Effect of Bandgap Lowering by C60 on a Conjugated Polymer" Adv. Mater. 2005, 17, 897-900. Date of web publication: Mar. 30, 2005.*
Murata et al., "100% Encapsulation of Hydrogen Molecule into an Open-Cage Fullerene Derivative and Gas-Phase Generation of $H_2@C_{60}$," J. Amer. Chem. Soc., vol. 125, pp. 7152-7153 (2003).
Taiwan Office Action for Taiwan Application No. 100118816 dated Nov. 5, 2013.
W. Qian et al., "Synthesis of Stable Derivatives of $C_{62}$: The first Nonclassical Fullerene Incorporating a Four-Membered Ring" J. Am. Chem. Soc.,2003, 125, pp. 2066-2067.
S. Chunag et al., "An Orifice-Size Index for Open-Cage Fullerenes" J. Org. Chem., 2007, 72, pp. 6447-6453.
S. Backer et al., "High Efficiency Organic Photovoltaics Incorporating a New Family of Soluble Fullerene Derivatives" Chem. Matter, 2007, 19, pp. 2927-2929.
Y. He et al., "Indene-$C_{60}$ Bisadduct: A New Acceptor for High-Performance" J. Am. Chem. Soc., 2010, 132, p. 1377-1382.

* cited by examiner

Primary Examiner — Andrew K Bohaty
(74) Attorney, Agent, or Firm — Muncy, Geissler, Olds & Lowe, P.C.

(57) ABSTRACT

Disclosed is a fullerene derivative having a formula of F-Cy, wherein F is an open-cage fullerene, and Cy is a chalcogenyl group. The fullerene derivative can be applied to hydrogen storage material and an optoelectronic device such as an organic light emitting diode (OLED), a solar cell, or an organic thin film transistor (TFT).

4 Claims, 1 Drawing Sheet

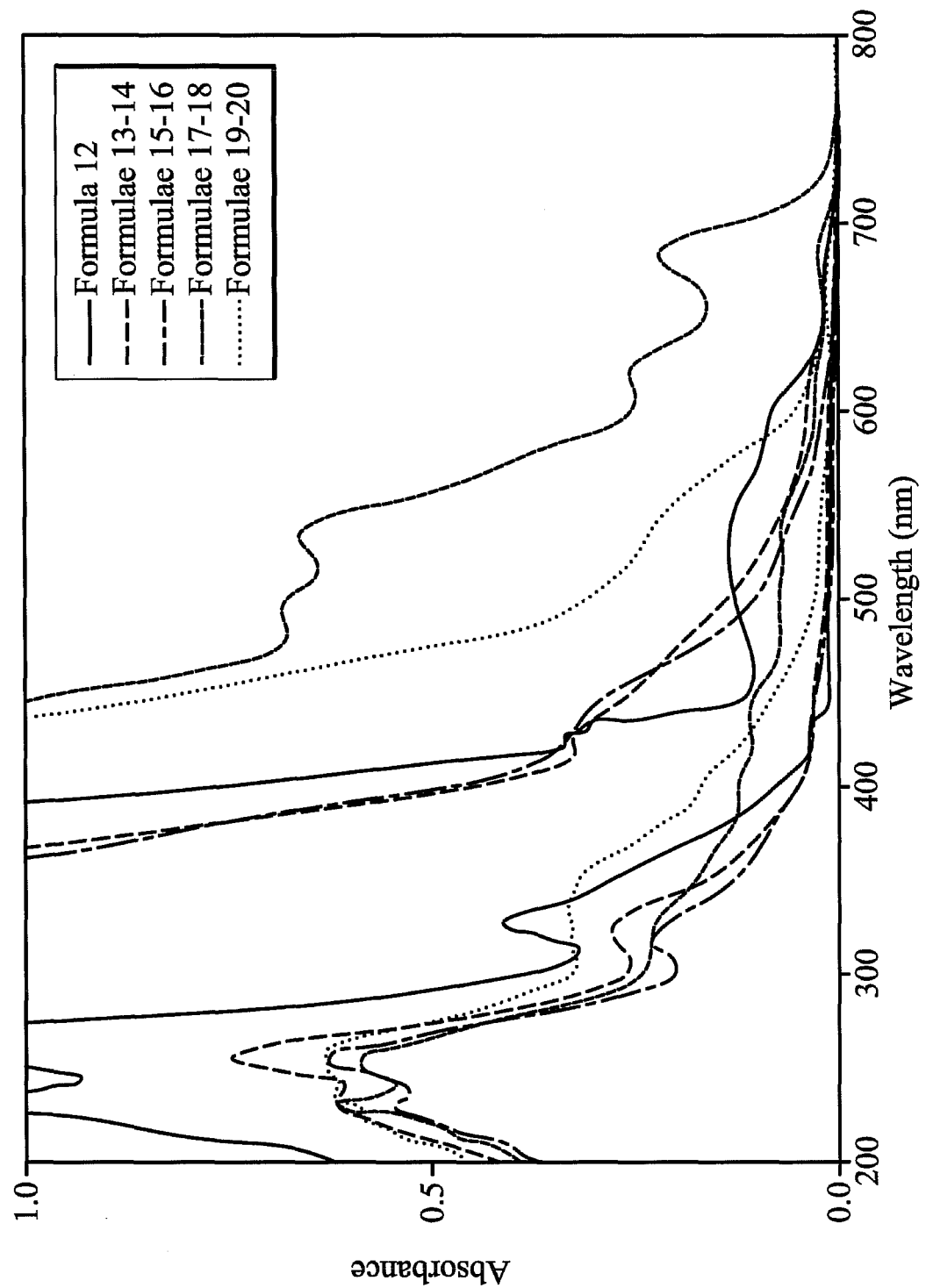

FULLERENE DERIVATIVES AND OPTOELECTRONIC DEVICES UTILIZING THE SAME

CROSS REFERENCE TO RELATED APPLICATIONS

This application claims priority of Taiwan Patent Application No. 100118816, filed on May 30, 2011, the entirety of which is incorporated by reference herein.

BACKGROUND OF THE INVENTION

1. Field of the Invention

The present disclosure relates to open-cage fullerene, and in particular relates to optoelectronic devices utilizing the same.

2. Description of the Related Art

An environmental friendly material with lighter weight is a major topic in the current solar cell field. Thin film materials have several advantages, such as light weights, flexibility, low costs, low temperature processibility, and large area manufacturing, and are suitable to be applied to an active layer of solar cells. The main type of active layer currently used is a combination of a p-type P3HT (poly(3-hexylthiophene)) and n-type $PC_{61}BM$ ([6,6]-phenyl C61-methyl butyrate) active layer. Accordingly, a novel combined material for enhancing energy conversion efficiency of solar cells is still called-for.

BRIEF SUMMARY OF THE INVENTION

One embodiment of the disclosure provides a fullerene derivative, having a formula: F-Cy; wherein F is an open-cage fullerene, and Cy is a chalcogenyl group.

One embodiment of the disclosure provides an optoelectronic device, comprising: an anode; a cathode; and an active layer disposed between the anode and the cathode, wherein the active layer comprises the described fullerene derivative.

A detailed description is given in the following embodiments with reference to the accompanying drawings.

BRIEF DESCRIPTION OF THE DRAWINGS

The present invention can be more fully understood by reading the subsequent detailed description and examples with references made to the accompanying drawings, wherein:

FIG. 1 shows UV-VIS absorbance spectra of chloroform solutions of open-cage fullerenes in embodiments of the disclosure.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

The disclosure is about fullerene derivatives having a formula F-Cy. F is an open-cage fullerene, and Cy is a chalcogenyl group. The chalcogenyl group is a hetero-cycle including a hetero atom selected from oxygen, sulfur, or selenium. The open-cage fullerene F can be open-cage $C_{60-84}$. In one embodiment, the open-cage fullerene F is open-cage $C_{60}$. The chalcogenyl group Cy can be saturated or unsaturated. In one embodiment, the chalcogenyl group is thiophene.

The open-cage fullerene derivative can be applied to a hydrogen storage material or an optoelectronic device such as an organic light emitting diode (OLED), a solar cell, or an organic thin film transistor. For example, the optoelectronic device may include an active layer disposed between a cathode and an anode, and the active layer may include the described open-cage fullerene derivative.

In one embodiment, the fullerene derivative can be synthesized as below. As shown in Formula 1,3,6-di(thiophen-2-yl)-1,2,4,5-tetrazine and alkene are reacted. In Formula 1, X is oxygen, sulfur, or selenium. R is —$(CH_2)_n$—Y, n is an integer of 1 to 10, and Y is selected from an ester group, an amide group, an aromatic group, an ether group, an aldehyde group, a ketone group, a hydroxyl group, a carboxylic acid group, halogen, an amino group, a sulfonic acid group, a sulfonate group, a phosphoric acid group, or a phosphate group. In other embodiments, the substituent groups on two sides of the terazine can be other chalcogenyl groups such as furan, thiophene, selenophen, oxazole, thiazole, isoxazole, benzofuran, isobenzofuran, benzothiophene, benzoxazole, benzoisoxazole, or benzothiazole.

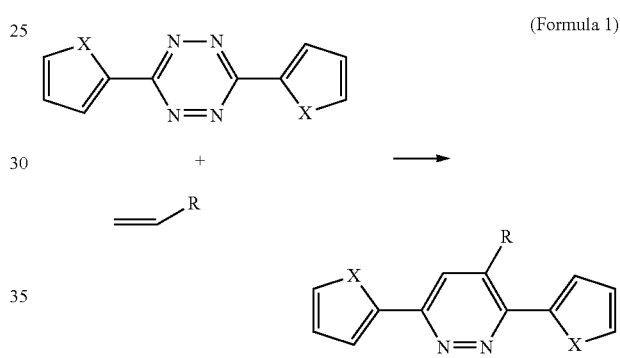

(Formula 1)

Subsequently, the product in Formula 1 is further reacted with a fullerene to form an open-cage fullerene derivative. In one embodiment, the fullerene is $C_{60}$, wherein a product obtained by the described reaction is shown in Formula 2. It should be understood that the open-cage fullerene derivative will have a larger ball size when the fullerene is $C_{70}$ or $C_{80}$ other than $C_{60}$, and the opened ring will still be an eight member ring after the reaction as shown in the bold line in Formula 2. The R and X in Formula 2 are similar to that in Formula 1.

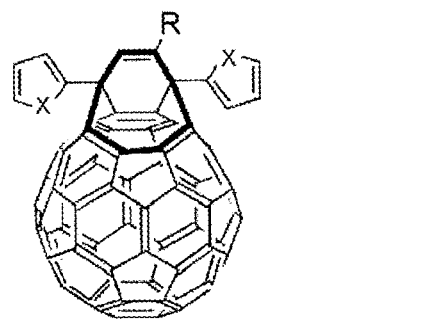

(Formula 2)

The open-cage fullerene derivative can be oxidized to expand the opened ring from the eight member ring to a twelve member ring. In one embodiment, the open-cage fullerene derivative in Formula 2 is oxidized to obtain the products in Formulae 3 and 4. The R and X in Formulae 3 and 4 are similar to that in Formula 1.

(Formula 3)

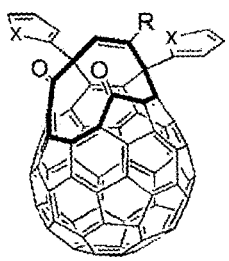

(Formula 4)

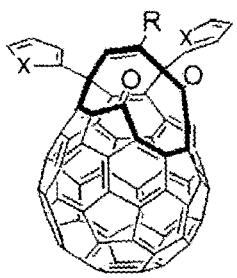

The oxidized open-cage fullerene derivative can be reacted with sulfur powder and tetrakis(dimethylamino)ethylene to expand the opened ring from the twelve member ring to a thirteen member ring. In one embodiment, the open-cage fullerene derivatives in Formulae 3 and 4 are reacted with sulfur powder and tetrakis(dimethylamino)ethylene to obtain the products in Formulae 5 and 6. The R and X in Formulae 5 and 6 are similar to that in Formula 1.

(Formula 5)

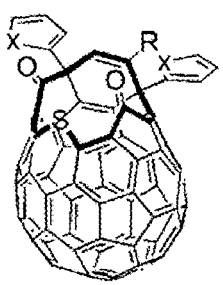

(Formula 6)

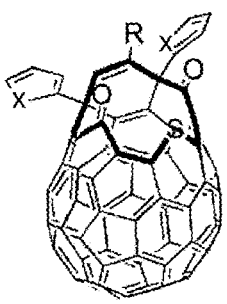

The oxidized open-cage fullerene derivative can be reacted with phenylhydrazine and pyridine to expand the opened ring from the twelve member ring to a sixteen member ring. In one embodiment, the open-cage fullerene derivatives in Formulae 3 and 4 are reacted with phenylhydrazine and pyridine to obtain the products in Formulae 7 and 8. The R and X in Formulae 7 and 8 are similar to that in Formula 1.

(Formula 7)

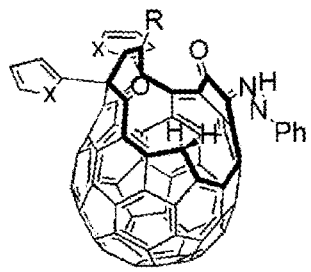

(Formula 8)

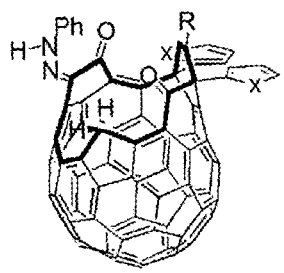

The oxidized open-cage fullerene derivative can be reacted with o-phenylenediamine and pyridine to expand the opened ring from the twelve member ring to a twenty member ring. In one embodiment, the open-cage fullerene derivatives in Formulae 3 and 4 are reacted with o-phenylenediamine and pyridine to obtain the products in Formulae 9 and 10. The R and X in Formulae 9 and 10 are similar to that in Formula 1.

(Formula 9)

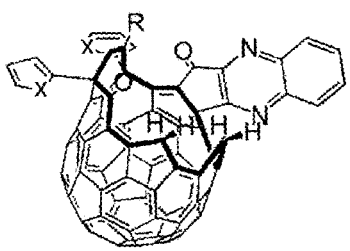

(Formula 10)

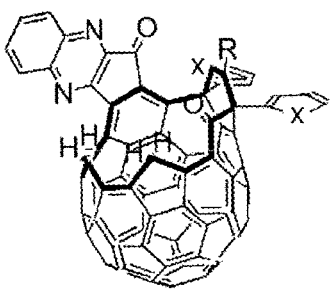

EXAMPLES

Preparation Example 1

As shown in Formula 11, a mixture of 3,6-di(thiophen-2-yl)-1,2,4,5-tetrazine (1.18 g, 0.0048 mmol) and ethyl 6-heptenoate (0.99 g, 0.0064 mmol) in o-xylene (30 mL) was heated at 140° C. for 24 h in a high pressure tube. The resulting light orange solution was then bubbled with oxygen for 15 minutes and heated for another 24 hours. The resulting mixture was purified by silica gel chromatography using hexanes/ethyl acetate=1/1 to give a product (816 mg, 46%) as a pale yellow solid (mp/99-101° C.); $R_f$=0.45 (hexanes/ethyl acetate). $^1$H NMR (300 MHz, CDCl$_3$, δ) 7.71-7.73 (m, 1H, CH), 7.63 (s, 1H, CH), 7.48-7.55 (m, 3H, CH), 7.16-7.20 (m, 2H, CH), 4.14 (q, J=7.2 Hz, 2H, CH$_2$), 2.94-2.99 (m, 2H, CH$_2$), 2.36-2.41 (m, 2H, CH$_2$), 1.77-1.82 (m, 4H, CH$_2$), 1.26 (t, J=7.2 Hz, 3H, CH$_3$); $^{13}$C NMR (75 MHz CDCl$_3$, δ) 173.1 (C=O), 153.5, 152.6, 140.4, 140.3, 138.2, 128.8, 128.6, 127.9, 127.8, 127.6, 125.9, 122.2, 60.3, 33.7, 32.4, 27.8, 24.4, 14.1; FTIR (KBr) υ=(cm$^{-1}$) 1730 (s, C=O); EI-MS, calcd for $C_{19}H_{20}N_2O_2S_2$ 372. found 372 (81), 271 (100).

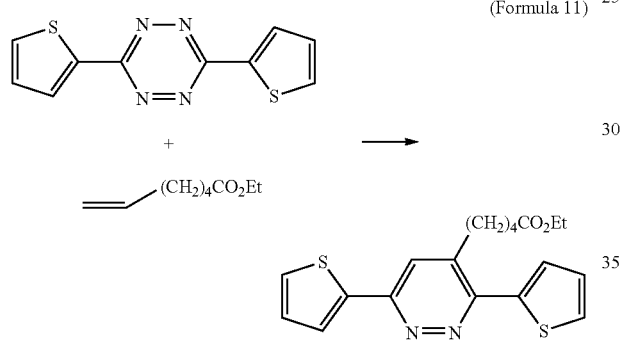

(Formula 11)

Example 1

A mixture of fullerene C$_{60}$ (316 mg, 0.439 mmol) and the product of Formula 11 (260 mg, 0.699 mmol) in 50 mL of 1-chloronaphthalene was refluxed at 270° C. for 48 h under argon. The resulting reddish-purple solution was purified by flash chromatography using toluene/hexanes=2:1 to give unreacted C$_{60}$ (170 mg, 34%) and then toluene as eluent to give product (188 mg, 39%; 85% based on converted C$_{60}$) as a brown solid as shown in Formula 12. $R_f$=0.5 (toluene). $^1$H NMR (300 MHz, CDCl$_3$, δ) 7.40-7.50 (m, 4H, CH), 7.11-7.14 (m, 2H, CH), 6.13 (s, 1H, CH), 4.11 (q, J=7.2 Hz, 2H, CH$_2$), 2.25 (t, J=7.2 Hz, 2H, CH$_2$), 1.83-2.18 (m, 3H, CH$_2$), 1.33-1.45 (m, 3H, CH$_2$), 1.21 (t, J=7.2 Hz, 3H, CH$_3$); $^{13}$C NMR (125 MHz, CDCl$_3$, δ) 173.49 (C=O), 154.00, 151.95, 150.33, 149.76, 149.23, 145.89, 145.77*, 145.41, 145.37, 145.02, 144.97, 144.71, 144.56, 144.50, 144.43, 144.41, 144.24, 144.20*, 144.15*, 144.07*, 144.04, 143.82*, 143.75, 143.72, 143.64, 143.48*, 142.38, 142.15, 140.88*, 140.76, 140.70, 140.64*, 140.63*, 140.58, 140.18, 140.10, 138.25, 138.08, 137.82, 137.17, 137.07, 136.86, 135.46, 135.28, 135.11, 134.90, 134.81, 134.57, 129.84, 127.83, 127.54, 127.39, 126.73, 126.44, 126.31, 126.18, 125.86, 125.71, 125.20, 125.04, 124.67, 60.26, 54.37, 51.50, 34.06, 33.10, 27.51, 24.70, 14.27 (asterisked peaks may be two overlapping carbons signals due to their twice-fold intensity as compared to other carbon signals; FTIR (KBr) υ=(cm$^{-1}$) 1730 (s, C=O); MALDI-TOF MS, calcd for $C_{79}H_{20}O_2S_2$ 1064.1. found 1064.0. The compound in Formula 12 was dissolved in chloroform to measure its UV-VIS absorbance spectrum, as shown in FIG. 1. In addition, the chloroform solution of the compound in Formula 12 can be analyzed by cyclic voltammetry (CV) to calculate its HOMO (−5.64 eV), LUMO (−3.73 eV), and energy gap (1.90 eV).

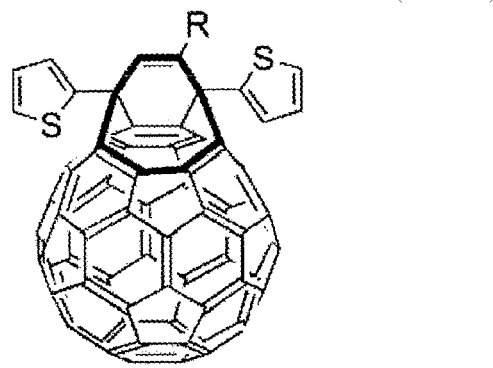

(Formula 12)

Example 2

A solution of the compound in Formula 12 (115 mg, 0.071 mmol) in CS$_2$ (115 mL) was irradiated by a halogen-lamp (500 Watt) from a distance of 30 cm for 3 hours under oxygen. The resulting dark brown solution was purified by silica gel chromatography using toluene as eluent to provide a mixture (79 mg, 67%) as a brown solid of Formulae 13 and 14 (60:40). In Formulae 13 and 14, R is —(CH$_2$)$_4$CO$_2$Et. $R_f$=0.15 (toluene). $^1$H NMR (300 MHz, CDCl$_3$, δ) 7.32-7.37 (m, 4H, CH), 7.10-7.22 (m, 4H, CH), 6.99-7.04 (m, 4H, CH), 6.83 (s, CH), 6.60 (s, CH), 4.16 (q, J=7.2 Hz, 4H, CH$_2$), 3.29-3.39 (m, 1H, CH$_2$), 2.90-2.98 (m, 1H, CH$_2$), 2.56-2.63 (m, 1H, CH$_2$), 2.37 (t, J=6.6 Hz, 4H, CH$_2$), 1.94-2.11 (m, 1H, CH$_2$), 2.20-2.29 (m, 1H, CH$_2$), 1.67-2.01 (m, 4H, CH$_2$), 1.40-1.47 (m, 2H, CH$_2$), 1.29 (t, J=7.2 Hz, 6H, CH$_3$), 0.85-0.96 (m, 1H, CH$_2$); FTIR (KBr) υ=(cm$^{-1}$) 1633 (s, C=O), 1741 (s, C=O); MALDI-TOF MS, calcd for $C_{79}H_{20}O_4S_2$ 1096.1. found 1096.8. The compounds in Formulae 13 and 14 were dissolved in chloroform to measure its UV-VIS absorbance spectrum, as shown in FIG. 1. In addition, the chloroform solution of the compounds in Formulae 13 and 14 can be analyzed by cyclic voltammetry (CV) to calculate its HOMO (−5.71 eV), LUMO (−3.97 eV), and energy gap (1.74 eV).

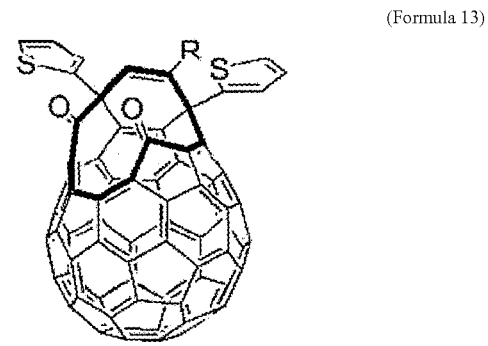

(Formula 13)

(Formula 14)

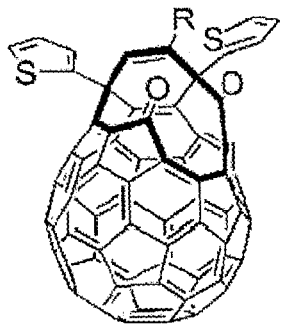

(Formula 16)

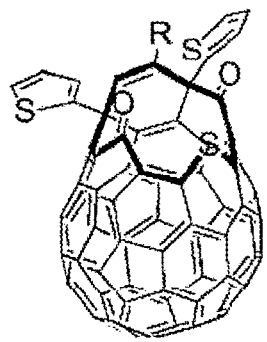

Example 3

A brown solution of the mixture of the compounds in Formulae 13 and 14 (21 mg, 0.019 mmol) and powdered sulfur (25 mg, 0.097 mmol) in dry o-dichlorobenzene (ODCB, 15 mL) under argon was added tetrakis(dimethylamino)ethylene (33.0 μL, 0.137 mmol) at 180° C. The resulting mixture was stirred at 180° C. for 10 minutes. The color of the mixture slowly turned dark red-brown. The resulting dark red-brown solution was passed through the silica gel chromatography using toluene as eluent to provide a mixture (20 mg, 91%) as a reddish brown solid of Formulae 15 and 16 (60:40). In Formulae 15 and 16, R is —$(CH_2)_4CO_2Et$. $R_f$=0.29 (toluene). $^1$H NMR (300 MHz, $CDCl_3$, δ) 7.22-7.34 (m, 4H, CH), 6.99-7.19 (m, 4H, CH), 6.80-6.92 (m, 4H, CH), 6.76 (s, 1H, CH), 6.56 (s, 1H, CH), 4.15 (q, J=6.9 Hz, 4H, $CH_2$), 3.26-3.40 (m, 2H, $CH_2$), 2.83-3.05 (m, 2H, $CH_2$), 2.33 (t, J=6.6 Hz, 4H, $CH_2$), 1.90-2.25 (m, 2H, $CH_2$), 1.62-1.73 (m, 6H, $CH_2$), 1.28 (t, J=7.2 Hz, 6H, $CH_3$); FTIR (KBr) ν=($cm^{-1}$) 1699 (s, C=O), 1737 (s, C=O); MALDI-TOF MS, calcd for $C_{79}H_{20}O_4S_3Na$ (M+Na$^+$) 1151.0. found 1151.4. The mixture of the compounds in Formulae 15 and 16 were dissolved in chloroform to measure its UV-VIS absorbance spectrum, as shown in FIG. 1. In addition, the chloroform solution of the mixture of the compounds in Formulae 15 and 16 can be analyzed by cyclic voltammetry (CV) to calculate its HOMO (−5.72 eV), LUMO (−3.77 eV), and energy gap (1.95 eV).

Example 4

A brown solution of the mixture of the compounds in Formulae 13 and 14 (30 mg, 0.027 mmol) and phenylhydrazine (3.1 mg, 0.029 mmol) in ODCB (3 mL) under argon was added pyridine (13.1 μL, 0.163 mmol) at room temperature. The resulting mixture was stirred at 65° C. for 2 hours. The color of the mixture slowly turned dark black. The resulting dark black solution was purified by silica gel chromatography using toluene as an eluent to obtain a mixture (16 mg, 49%) as a black solid of Formulae 17 and 18 (57:43). In Formulae 17 and 18, R is —$(CH_2)_4CO_2Et$. $R_f$=0.48/0.55 (toluene). $^1$H NMR (300 MHz, $CDCl_3$, δ) 13.83 (s, 1H, NH), 13.72 (s, 11-1, NH), 7.75-7.82 (m, 4H, CH), 7.56-7.60 (m, 4H, CH), 7.11-7.38 (m, 6H, CH), 6.98-7.06 (m, 4H, CH), 6.83-6.93 (m, 4H, CH), 6.60 (s, 1H, CH), 6.47 (s, 1H, CH), 5.32 (m, 2H, $CH_2$), 4.86 (m, 2H, $CH_2$), 5.32 (d, J=20.4, 1H, $CH_2$), 5.31 (d, J=20.4, 1H, $CH_2$), 4.83 (d, J=20.4, 1H, $CH_2$), 4.80 (d, J=20.4, 1H, $CH_2$), 4.16-4.23 (m, 4H, $CH_2$), 2.81-3.09 (m, 4H, $CH_2$), 2.32-2.42 (m, 4H, $CH_2$), 1.83-2.07 (m, 4H, $CH_2$), 1.60-1.72 (m, 4H, $CH_2$), 1.27-1.34 (m, 6H, $CH_3$), 0.87-1.25 (m, 4H, $C_{1-12}$); FTIR (KBr) ν=($cm^{-1}$) 1681 (s, C=O), 1731 (s, C=O); MALDI-TOF MS, calcd for $C_{85}H_{28}N_2O_4S_2$ 1204.1. found 1204.5. The mixture of the compounds in Formulae 17 and 18 were dissolved in chloroform to measure its UV-VIS absorbance spectrum, as shown in FIG. 1. In addition, the chloroform solution of the mixture of the compounds in Formulae 17 and 18 can be analyzed by cyclic voltammetry (CV) to calculate its HOMO (−5.44 eV), LUMO (−3.72 eV), and energy gap (1.72 eV).

(Formula 15)

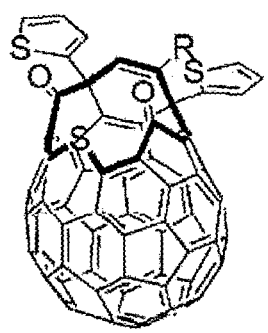

(Formula 17)

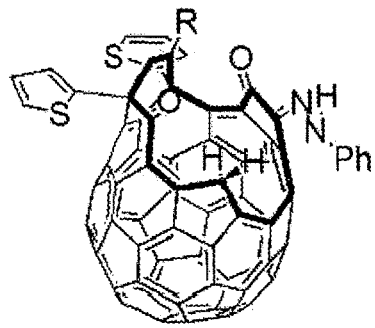

-continued (Formula 18)

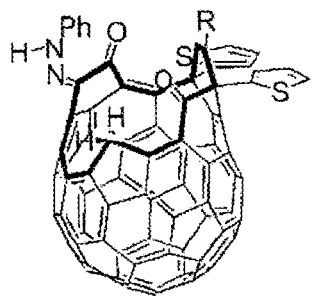

Example 5

A brown solution of the mixture of the compounds in Formulae 13 and 14 (30 mg, 0.027 mmol) and o-Phenylenediamine (15 mg, 0.139 mmol) in ODCB (3 mL) under argon was added pyridine (106 μL, 1.35 mmol) at room temperature. The resulting mixture was stirred at 65° C. for 12 hours. The color of the mixture slowly turned dark brown. The resulting solution was purified by silica gel chromatography using eluent of toluene/ethyl acetate=10/1 to give mixture (22 mg, 68%) as a brown solid of the compounds in Formulae 19 and 20 (51:49). In Formulae 19 and 20, R is —(CH$_2$)$_4$CO$_2$Et. $R_f$=0.38/0.45 (toluene/ethyl acetate=10/1). $^1$H NMR (300 MHz, CDCl$_3$, δ) 8.29-8.49 (m, 4H, CH), 7.91-7.97 (m, 4H, CH), 7.18-7.30 (m, 4H, CH), 7.25-7.30 (m, CH), 6.88-7.06 (m, 9H, CH), 6.21 (s, 1H, CH), 4.46-4.68 (m, 4H, CH$_2$), 4.10-4.16 (m, 4H, CH$_2$), 3.35-3.65 (m, 2H, CH$_2$), 2.90-3.04 (m, 2H, CH$_2$), 2.80-2.95 (m, 1H, CH$_2$), 2.54-2.62 (m, 1H, CH$_2$), 2.24-2.35 (m, 6H, CH$_2$), 1.61-2.13 (m, 4H, CH$_2$), 1.22-1.29 (m, 6H, CH$_3$), 0.86-1.20.98 (m, 4H, CH$_2$), −11.28 (s, H$_2$O), −11.34 (s, H$_2$O); FTIR (KBr) υ=(cm$^{-1}$) 1682 (s, C=O), 1730 (s, C=O); MALDI-TOF MS, calcd for C$_{85}$H$_{28}$N$_2$O$_4$S$_2$ 1204.1. found 1204.6. The mixture of the compounds in Formulae 19 and 20 were dissolved in chloroform to measure its UV-VIS absorbance spectrum, as shown in FIG. 1. In addition, the chloroform solution of the mixture of the compounds in Formulae 19 and 20 can be analyzed by cyclic voltammetry (CV) to calculate its HOMO (−5.54 eV), LUMO (−3.81 eV), and energy gap (1.74 eV).

(Formula 19)

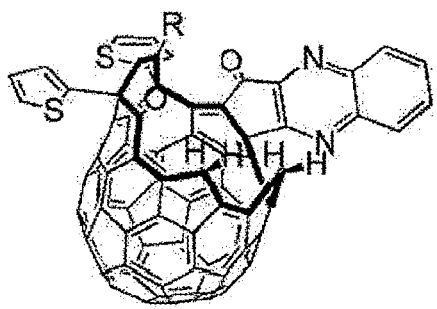

-continued (Formula 20)

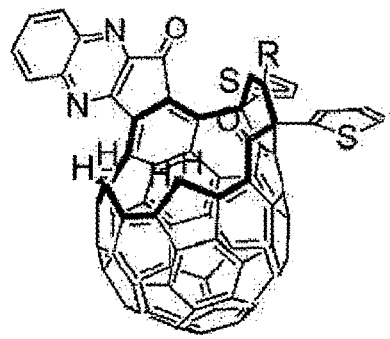

Example 6

All BHJ photovoltaic devices were prepared with the same procedures. The device fabrication procedures are described below: the glass-indium tin oxide (ITO) substrates (obtained from Sanyo, Japan (8Ω/□)) were first patterned by lithography, then cleaned with detergents, and ultrasonicated in acetone and isopropyl alcohol and subsequently dried on a hot plate at 120° C. for 5 minutes, and finally treated with oxygen plasma for 5 minutes. Poly(3,4-ethylene-dioxythiophene): poly(styrenesulfonate) (PEDOT:PSS, Baytron P-VP AI4083) was filtered through a 0.45 μm filter before being deposited on an ITO, with a thickness around 30 nm, by spin coating at 3000 rpm in the air and dried at 150° C. for 30 minutes inside of a glove box. C$_{60}$ and the open-cage fullerene derivatives in Formulae 12, 13-14, 15-16, 17-17, and 19-20 at a concentration of 15 mg/mL, were dissolved in o-DCB solution of P3HT (commercially available from Aldrich, see Formula 21, n is 90 to 400) at a concentration of 15 mg/mL, respectively, and then spun on the PEDOT-PSS film at a spin rate of 800 rpm to form active layers. The optimal thickness of the active layers obtained under the conditions was ca. 150 nm. Subsequently, the device was completed by coating a 30 nm-thick of Ca and an 80 nm thick of Al in <10$^{-6}$ mm-Hg pressure, respectively. The active area of the device was 5 mm$^2$. Finally the cell was encapsulated using UV-curing glue (obtained from Nagase, Japan). Upon device encapsulation, the OPV devices were measured in air, using a computer-controlled Keithley 2400 source measurement unit (SMU) equipped with a Peccell solar simulator under AM 1.5 G illumination (100 mWcm$^{-2}$) The performance of the solar cells having the different active layers composed of the n-type material (C$_{60}$ and compounds in Formulae 12-20) and the p-type material P3HT were tabulated in Table 1. As shown in Table 1, the solar cells utilizing the open-cage fullerene derivatives in Formulae 12-20 as the n-type material in the active layer had better short circuit current density (Jsc), filling factor (FF), power conversion efficiency (PCE), and electron mobility (μ$_e$) than the solar cell utilizing C$_{60}$ with the n-type material in the active layer.

(Formula 21)

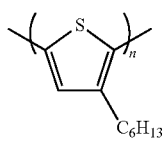

It should be understood that the open-cage fullerene derivatives having different HOMO and LUMO can be collocated with p-type materials other than P3HT for further improving the solar cell performance.

TABLE 1

| n-type material in the active layer | $J_{sc}$ | $V_{oc}$ (V) | FF | PCE (%) | $\mu_e$ (m$^2$/V s) |
|---|---|---|---|---|---|
| $C_{60}$ | 1.9 | 0.50 | 0.51 | 0.48 | $1.9 \times 10^{-7}$ |
| Formula 12 | 7.2 | 0.62 | 0.66 | 2.9 | $4.6 \times 10^{-8}$ |
| Formulae 13 and 14 | 5.3 | 0.40 | 0.62 | 1.3 | $1.9 \times 10^{-8}$ |
| Formulae 15 and 16 | 5.8 | 0.51 | 0.62 | 1.8 | $1.8 \times 10^{-8}$ |
| Formulae 17 and 18 | 4.9 | 0.65 | 0.51 | 1.6 | $1.4 \times 10^{-8}$ |
| Formulae 19 and 20 | 3.4 | 0.57 | 0.56 | 1.1 | $8.7 \times 10^{-9}$ |

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A fullerene derivative, having a formula:

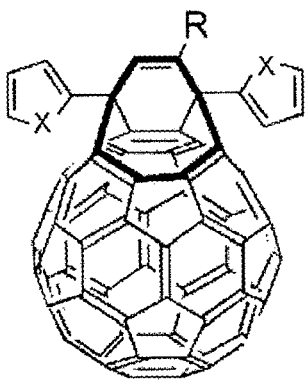

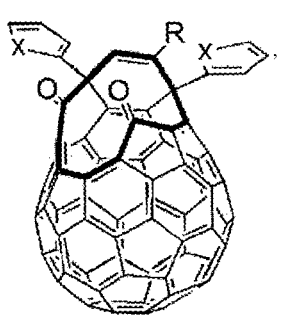

-continued

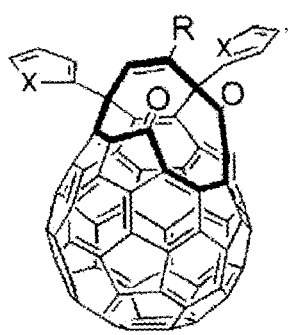

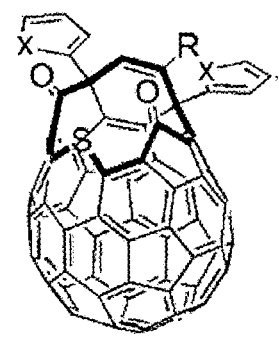

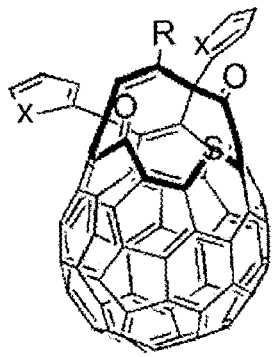

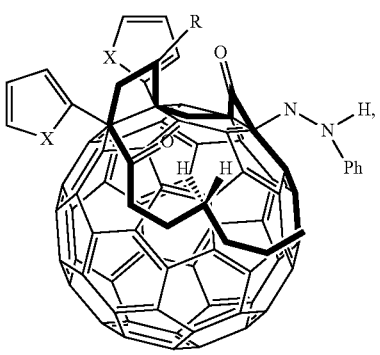

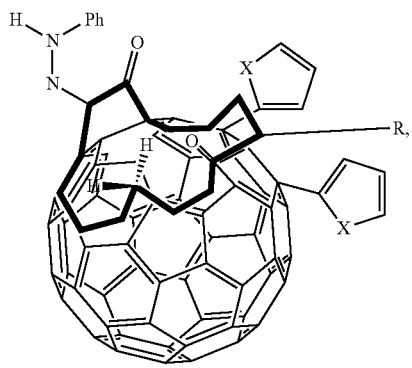

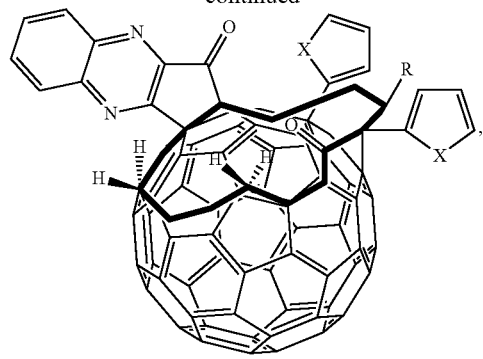

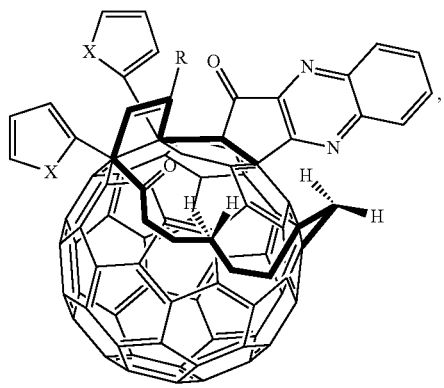

wherein X is selected from oxygen, sulfur, or selenium,

R is —$(CH_2)_n$—Y, wherein n is an integer of 1 to 10, and Y is selected from an ester group, an amide group, an aromatic group, an ether group, an aldehyde group, a ketone group, a hydroxyl group, a carboxylic acid group, halogen, an amino group, a sulfonic acid group, a sulfonate group, a phosphoric acid group, or a phosphate group; and Ph is an aromatic group.

2. The fullerene derivative as claimed in claim 1, being applied to a hydrogen storage material.

3. An optoelectronic device, comprising:
an anode;
a cathode; and
an active layer disposed between the anode and the cathode,
wherein the active layer comprises the fullerene derivative as claimed in claim 1.

4. The optoelectronic device as claimed in claim 3, comprising an organic light emitting diode, a solar cell, or an organic thin film transistor.

* * * * *